(12) United States Patent
Linares et al.

(10) Patent No.: US 10,639,452 B2
(45) Date of Patent: May 5, 2020

(54) ECHO-OPAQUE URETHRAL CATHETER

(75) Inventors: Luis Linares, Guatemala (GT);
Krishnan Suthanthiran, Lorton, VA (US); Manny R. Subramanian, Frederick, MD (US)

(73) Assignee: Best Medical International, Inc., Springfield, VA (US)

( * ) Notice: Subject to any disclaimer, the term of this patent is extended or adjusted under 35 U.S.C. 154(b) by 0 days.

(21) Appl. No.: 11/548,085

(22) Filed: Oct. 10, 2006

(65) Prior Publication Data

US 2011/0224538 A1    Sep. 15, 2011

Related U.S. Application Data

(60) Provisional application No. 60/807,296, filed on Jul. 13, 2006.

(51) Int. Cl.
| | |
|---|---|
| *A61B 6/00* | (2006.01) |
| *A61M 25/01* | (2006.01) |
| *A61B 8/08* | (2006.01) |
| *A61L 29/18* | (2006.01) |
| *A61L 29/02* | (2006.01) |
| *A61M 25/10* | (2013.01) |
| *A61B 6/12* | (2006.01) |
| *A61B 8/12* | (2006.01) |
| *A61M 25/00* | (2006.01) |
| *A61B 8/00* | (2006.01) |

(52) U.S. Cl.
CPC ....... *A61M 25/0108* (2013.01); *A61B 8/0841* (2013.01); *A61L 29/02* (2013.01); *A61L 29/18* (2013.01); *A61B 6/12* (2013.01); *A61B 8/12* (2013.01); *A61B 8/445* (2013.01); *A61M 25/0043* (2013.01); *A61M 25/10* (2013.01); *A61M 2210/166* (2013.01)

(58) Field of Classification Search
None
See application file for complete search history.

(56) References Cited

U.S. PATENT DOCUMENTS

| | | | | |
|---|---|---|---|---|
| 4,838,876 | A | * | 6/1989 | Wong et al. ................... 604/265 |
| 5,007,900 | A | | 4/1991 | Picha et al. |
| 5,454,788 | A | | 10/1995 | Walker et al. |
| 5,520,646 | A | | 5/1996 | D'Andrea |
| 5,916,143 | A | | 6/1999 | Apple et al. |
| 5,921,933 | A | * | 7/1999 | Sarkis et al. .................. 600/459 |
| 5,954,715 | A | * | 9/1999 | Harrington et al. ............ 606/28 |
| 6,083,166 | A | | 7/2000 | Holdaway et al. |

(Continued)

*Primary Examiner* — Jonathan Cwern (57) ABSTRACT

A urethral catheter and its method of use to identify a patient's urethral anatomic course for the precise placement of a treatment element into the patient's prostate are provided. An echo-opaque urethral catheter including an echogenic material and a radio-opaque material in at least an image portion thereof is introduced into a urethra until its echogenic and radio-opaque image portion is generally aligned with a treatment site of the prostate. An image probe positioned relative to the treatment site is activated to obtain a real time image of the prostate and urethra by ultrasound or X-ray imaging. The echo-opaque urethral catheter includes an elongated flexible catheter, at least the image portion of which, is coated with, incorporates within or is enclosed by the echogenic and radio-opaque materials that enhance ultrasound and radio visualization.

26 Claims, 5 Drawing Sheets

(56) References Cited

U.S. PATENT DOCUMENTS

| | | |
|---|---|---|
| 6,217,518 B1 | 4/2001 | Holdaway et al. |
| 6,356,782 B1 * | 3/2002 | Sirimanne et al. ............ 600/431 |
| 6,533,763 B1 * | 3/2003 | Schneiter ............ A61M 25/007 |
| | | 604/264 |
| 6,547,785 B1 | 4/2003 | Heiner et al. |
| 6,582,368 B2 | 6/2003 | Holdaway et al. |
| 6,726,651 B1 * | 4/2004 | Robinson et al. ....... 604/101.01 |
| 6,863,654 B2 | 3/2005 | Zappala et al. |
| 2001/0007081 A1 | 7/2001 | Caprio et al. |
| 2002/0068853 A1 | 6/2002 | Adler |
| 2002/0077593 A1 | 6/2002 | Perkins et al. |
| 2002/0099289 A1 | 7/2002 | Crowley |
| 2002/0111617 A1 * | 8/2002 | Cosman et al. ................ 606/41 |
| 2004/0073158 A1 * | 4/2004 | Shah et al. ...................... 604/19 |
| 2004/0176747 A1 * | 9/2004 | Feneley ............ A61M 25/0017 |
| | | 604/544 |
| 2004/0225216 A1 * | 11/2004 | Zappala et al. ............... 600/439 |
| 2005/0203400 A1 | 9/2005 | Zappala et al. |

* cited by examiner

FIG.1

ECHO-OPAQUE URETHRAL CATHETER

CROSS-REFERENCE

This application claims priority to Provisional Application No. 60/807,296, filed Jul. 13, 2006, the entire content of which is hereby incorporated by reference.

BACKGROUND

The present invention relates to identifying a patient's anatomic urethra course and treatment devices. The invention is especially suited for accurately locating a brachytherapy or cryoablation treatment element inside a patient's prostate thereby allowing a practitioner to achieve optimal spacing between the treatment element and the urethra, while still positioning the treatment element in effective and operative proximity to a tumor, Benign Prostatic Hyperplasia (BPH) tissue, or other desired treatment site within the prostate. In this regard, the present invention is further directed towards a urethra identification system and more specifically an echo-opaque catheter, which substantially enhances the identification of the urethra at the prostate by generating, acoustic or visual interface that is effectively visible utilizing common diagnostic modality such as ultrasound equipment or X-ray machine. As a result, utilizing the present system and method, a physician can take into account the possible detrimental effects of locating treatment elements, such as radioactive seeds and/or cryo-probes, too close to the urethra itself, while still appropriately positioning the treatment element to effectively treat or affect a tumor, BPH tissue or other treatment site. Although, urethra identification is used as an example, the present system and method may also be used in the identification of other similar anatomic structures, such as female urethra for GYN structures.

Radiation therapy involves medical procedures that selectively expose certain areas of a human body, such as cancerous tumors, to high doses of radiation. The prostate is a male accessory sex organ located inferior to the urinary bladder and anterior to the rectum. Roughly the size of a walnut, the prostate is located in generally close proximity to the urinary bladder and surrounds and/or encircles an upper part of the urethra, the tube that is connected to the urinary bladder and empties urine therefrom. Prostate cancer is potentially aggressive and is the second leading cause of cancer deaths among men in the United States. When diagnosed at an early, localized stage and when the disease is organ confined, prostate cancer is also often considered one of the most treatable and curable forms of cancer. As a result, early detection and effective treatment are of a critical nature.

Over the years a variety of different techniques and procedures have been developed in an effort to effectively treat prostate cancer, as well as other disorders associated with the prostate, including, but not limited to Benign Prostatic Hyperplasia (BPH). Specifically, in addition to traditional radiation/chemotherapy treatments, which are commonly employed for a variety of different types of cancer, due to the localized nature of prostate cancer, if detected sufficiently early, a variety of additional techniques to treat prostate tumors have been developed.

One of the existing treatment procedures involves the complete removal of the prostate from the patient and/or the resection of affected portions of the prostate. Given the nature of a malignant tumor, when surgery is the elected course of treatment, complete removal of the prostate is generally undertaken. However, in many circumstances surgery for the removal of a prostate may not be desirable for a variety of reasons. Among these are the postoperative risks of urinary incontinence and erectile dysfunction, and co-morbid medical conditions, which may increase a patient's morbidity and/or intra-operative mortality. The anatomic location of the prostate, in relation to the external urinary sphincter and the lateral neurovascular bundles, mandates that extirpative surgical procedures for the prostate maintain the integrity of the external urinary sphincter and preserve the neural erectile pathways. Therefore, it may be preferable to leave the prostate intact. As a result, alternative minimally invasive techniques, which treat prostate malignancies, but do not require removal of the prostate, may ultimately be the preferred course of treatment, and such treatment protocols are continuously being perfected.

In particular, there exist a variety of novel techniques, which do not require a patient to be subjected to excessive doses of radiation, but which perform substantially localized treatment directly to the prostate. One such technique known as transperineal interstitial brachytherapy ("brachytherapy") is commonly utilized when managing localized prostate cancer. Specifically, brachytherapy involves the transperineal delivery of radioactive implants, sometimes referred to as seeds, into the stroma of the prostate and in substantially close proximity to the tumor, for an extended period of time. In this regard, the one or more radioactive seeds can directly and/or locally treat a malignant tumor, often ultimately destroying the tumor, with limited effects to the rest of the patient's body. Another type of transperineal interstitial brachytherapy is the placement of needles around the prostate to delivery high dose radiation (HDR), using high activity radioactive wires.

Still another technique of localized treatment of a malignant tumor in the prostate, as well as the treatment of BPH, a condition whereby prostatic hypertrophy can result in an impediment to the evacuation of urine through the urethra, involve a treatment method known as cryoablation of the prostate. Under such cryoablation techniques, one or more cryo-probes and temperature sensing probes are introduced into the prostate into operative proximity with the malignant tumor or the desired treatment site. Specifically, the cryo-probes often include small gauge needles that can be effectively inserted into the prostate from the exterior of the patient. Through these cryo-probes, a cold temperature is effectively delivered at the treatment site, such as the site of the tumor, such as through the delivery of a cryogen gas including argon gas. Once the cryogen is delivered, a field of cold temperature is generated that forms essentially an ice ball to contain a majority of the lethal portions of the tumor, and/or to shrink the prostate. Subsequently, these ice balls are allowed to thaw, and then one or more subsequent freeze/thaw cycles can be performed in an effort to effectively cure the malignancy of the tumor and/or relieve the pressure resulting from the BPH.

In addition to the above techniques for localized treatment of a tumor and/or BPH and/or other ailments of the prostate, it is also recognized that other techniques are continuously being developed, refined and/or tested in an effort to achieve directed and localized treatment of tumors or other disorders within the prostate. Generally in such techniques, and especially in the techniques of brachytherapy and cryoablation, it is of significant importance for a practitioner to obtain an effective image of the prostate in order to identify a deposit location of the treatment element, be it radioactive seeds, after-loading needles in the case of HDR and/or cryo-probes, without performing highly invasive procedures. Traditionally, such imaging of the prostate is achieved utilizing transrectal ultrasonography or X-ray.

In particular, transrectal ultrasonography requires that a practitioner insert an ultrasound probe into the rectum, and utilizing the probe, direct ultrasound towards the prostate. When employing such an ultrasound system, the practitioner is thereby able to visualize an image of the prostate, on a monitor, in real time during the positioning of a treatment element. Unfortunately, while such techniques are generally effective for viewing the exterior shape and location of the walnut sized prostate; due to the inherent physical nature of the prostate and its circumferential orientation around the proximal urethra, practitioners typically cannot obtain any meaningful, sustained, and standardized imaging of the urethra, and more specifically the anatomic course of the prostatic urethra. Similar problems exist utilizing X-ray. Currently, a few techniques are used to generate a fleeting and inconsistent viewing of the urethra. Such techniques include the manual manipulation of a Foley catheter within the urethra or the introduction of an aerated gel into the catheter. Such techniques, however, cannot be readily controlled into a standardized and manageable on and off position, and generally provide merely a temporary, variable glimpse of the urethra, if any. Also, given the general desire to minimize the potential negative impact of the treatment elements, and especially the radioactivity from the radioactive seeds on the surrounding tissue and/or organs, the treatment elements have traditionally been implanted substantially into the prostate, such that the prostate itself would act as a shield for the external tissues and/or organs.

Although such practices had been traditionally accepted, more recent studies in brachytherapy have concluded that positioning of a treatment element in substantially close proximity to the urethra, such that the urethra is exposed to higher radiation doses, can correlate with urethral toxicity. The subsequent detrimental effects to the urethra may be clinically experienced as irritative voiding symptoms, urinary retention, and/or recto-urethral fistulas. Therefore, determining the precise location for the placement of the treatment element, such as radioactive seeds, needles for after-loading therapy and/or cryo-probes, relative to the urethra, can impact the nature, location, and quantity of treatment to be employed. As a result of these discoveries, it would be highly beneficial to provide a method and system which can effectively provide for the identification of the urethral course through the prostate, thereby allowing a practitioner, in real time, to effectively identify not only the external boundaries of the prostate, but also the urethra, thereby taking both into consideration when appropriately positioning a treatment element, such as radioactive seeds and/or cryo-probes. In particular, ideal techniques may call for a positioning of the treatment element in substantially close proximity to a malignant tumor, while maintaining a maximum possible spacing from the urethra.

U.S. Pat. No. 6,863,654 by Zappala et al. provides an attempt to identify urethral boundary in real time using ultrasound. The urethra identification system of Zappala comprises a tip bladder, an image bladder, a catheter and an imaging device. The tip bladder locates at the tip of the catheter and secures the device inside the patient. The image bladder is inflatable and is located around the portion of catheter that will be enclosed by the urethra. The image bladder is inflated with gas to allow contact with urethral wall. Under ultrasound, the practitioner is able to view and/or recognize the urethral boundaries within the prostate, as the primary item of importance related to appropriate viewing of the shape, size and location of the prostate so as to effectively achieve proper positioning of the treatment element within the prostate. In an alternative embodiment, hyperechogenic ring on the periphery of the catheter, which may create visible landmark images under ultrasound has been employed. However, the inflation of the image bladder may result in patient discomfort and cause the procedure to be more complicated. In addition, the invention does not support of detections using other image modality.

Presently, no identification systems and/or techniques provide for a clearly visible, less-painful and standardized visualization under all common image modality. As a result, the method and system of the present invention can provide a substantial enhancement in the field of art associated with localized treatment of tumors and other disorders, such as BPH, within the prostate in a manner, which reduces urethral exposure to the treatment element and thereby reduces postoperative complications to the urethra.

SUMMARY OF INVENTION

The present invention relates to a device and method of identifying a patient's urethra in real time, in order to facilitate the precise placement of a treatment element within the prostate in a desired location relative to the urethra. In particular, the present urethra identification device comprises a flexible elongated catheter with a primary lumen and a tip on its structured to be inserted into a patient's urethra into which is in fluid communication with a urinary bladder of the patient. Further, the elongate catheter will preferably have a sufficient length such that a tip of the catheter will actually extend into the urinary bladder of the patient. In a preferred embodiment, a marker is provided generally at the proximal tip of the elongate catheter. The tip marker may be made of hyper-echogenic and radio-opaque materials and may take a special form and shape, so that it would accurately indicate the position of the proximal end of the echo-opaque catheter during the device insertion and treating elements implantation. Additionally, a tip balloon may be provided near the proximal end of the echo-opaque catheter. This balloon is structured to be inflated once introduced into a patient's urinary bladder and thus secure the echo-opaque catheter within the patient.

The Echo-opaque catheter is structured to be at least partially echogenic and radio-opaque on its proximal portion so that an image device such as an X-ray Machine or an ultrasound device/screen, can image/see it, such as by X-ray imaging or ultrasound imaging, respectively. In a desired embodiment, the entire echo-opaque catheter is echogenic and radio-opaque, so an image of the portion of the urethra that is surrounded by a prostate can surely be seen on an image device. This design eliminates the guesswork associated with properly locating an image-generating portion of a catheter as described in the prior art.

The echogenicity of the catheter may be created by introducing bubbles into the walls of the echo-opaque catheter, using air or inert gases such as argon, helium, nitrogen etc. In the alternative, metallic chips may be incorporated into the walls of the entire or at least a portion of the echo-opaque catheter in order to generate distinct ultrasound images. Furthermore, sanded or corrugated metal wires or metal pieces may also be inserted into or placed outside of an echo-opaque catheter and thus generate landmark ultrasound images. The materials used may be metals or metal alloys of aluminum, stainless steel, copper, iron, silver, gold, cobalt, nickel etc. Ackley Metal Products (Santa Anna, Ca.) and Johnson Matthey (West Chester, Pa.) are two world leading companies that sell advanced technology materials.

The echogenicity of a catheter may also be enhanced by coating the surfaces of the walls of the echo-opaque catheter with echo-enhancing materials, such as magnesium, barium or special polymers. U.S. Pat. No. 6,749,554 by Snow et al. identifies a series of polymers that enhances ultrasound visibility. The coating may be deposited into a pattern such as stripes to further create a more distinct feature.

For X-ray visualization, radio-opaque materials may be used to form or coat the echo-opaque catheter. Chemical compounds with radio-opaque properties may be used, such as iodine, iohexol, iothalamate, ioxaglate, iopamidol, ioversaol, metriazimide, and/or diatrizoates. Duan Industries Inc. (Manchester, N.H.) and Limtech, Inc. (Sturtevant, Wis.) are two suppliers for these chemicals. In the alternative, metal or metal alloys with radio-opaque characteristics may also be used, such as those containing barium, magnesium, bismuth, lead, gold, tungsten, silver, platinum, palladium, iridium, rhodium. Ackley Metal Products (Santa Anna, Ca.) and Johnson Matthey (West Chester, Pa.) are two of world leading sellers for advanced technology materials including those required in this patent. Similarly, the radio-opaque materials may be incorporated into or used to coat the wall of the echo-opaque catheter. The coating or incorporation may form special patterns that would generate even more distinguishable images.

Because the some of the materials may enhance visualization of the catheter under both ultrasound and X-ray, it is preferred to use these materials. Also, the echogenic and/or radio-opaque coating materials may be deposited on the inside or outside surfaces of the catheter wall. The catheter may be made of any biocompatible polymers and may take the shape of the commonly used "Foley Catheter". Leco Plastics Inc. (Hackensack, N.J.) and LEFKO plastics products (Magog, QC, Canada) are well known manufacturers of catheters and plastic products. Alternatively, the catheter may be flexible and non-inflatable.

Further provided as a part of the urethra identification system is an imaging device. The imaging device may include an ultrasound type device with an imaging probe that is disposed in operative proximity to the patient's prostate and urethra. Preferably through the use of the imaging probe, the imaging device is structured to provide a real time image of a vicinity of the imaging probe and is structured to effectively view the echo-opaque catheter. The image device may also include an X-ray type device whose probe is placed around the patient near treatment site so to provide real-time images of the patient's anatomic structures and the echo-opaque catheter.

As a result of utilizing either type of image devices, a practitioner is able to effectively identify the urethra, as well as viewing the prostate before and during introduction of the treatment elements. Moreover, the process can generate a meaningful, manageable and standardized display for an extended period of time as needed by the practitioner.

From the preceding, it is seen that the present echo-opaque urethral catheter may be desirably utilized within a method of identifying a patient's urethral anatomic course, in real time for the precise placement of a treatment element into the patient's prostate. In particular, the method desirably includes an initial step of producing a urethral catheter that is elongated, flexible and with enhanced echogenicity and radio-opaque properties. Then, an imaging probe is operatively positioned relative to the treatment site of the prostate and the urethra. This imaging device will ultimately be activated so as to obtain a real time image of the treatment site of the prostate, such as on an associated monitor, which may be viewed by a practitioner. An echo-opaque urethral catheter would be inserted into the urethra until it reaches the urinary bladder. In one embodiment, the tip of the catheter is indicated by a tip marker, which is made with materials of enhanced echogenic and radio-opaque properties. With the echo-opaque urethral catheter appropriately positioned within the urethra of the patient with the tip marker placed within the bladder or at the bladder neck, the urethra can be thereafter identified during placement of the treatment element, and proper positioning of the treatment element relative to the urethra can be ensured. The method may further include a tip balloon. The tip balloon is located near the proximal end of the catheter and which is in fluid communication with the catheter. This tip balloon is inflated once the tip of the catheter reaches the urethral neck of the patient's bladder and therefore secures the catheter in position, avoiding any movement during the implantation of treatment elements.

These and other features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

DETAILED DESCRIPTION OF THE PREFERRED EMBODIMENT

Figure 1:
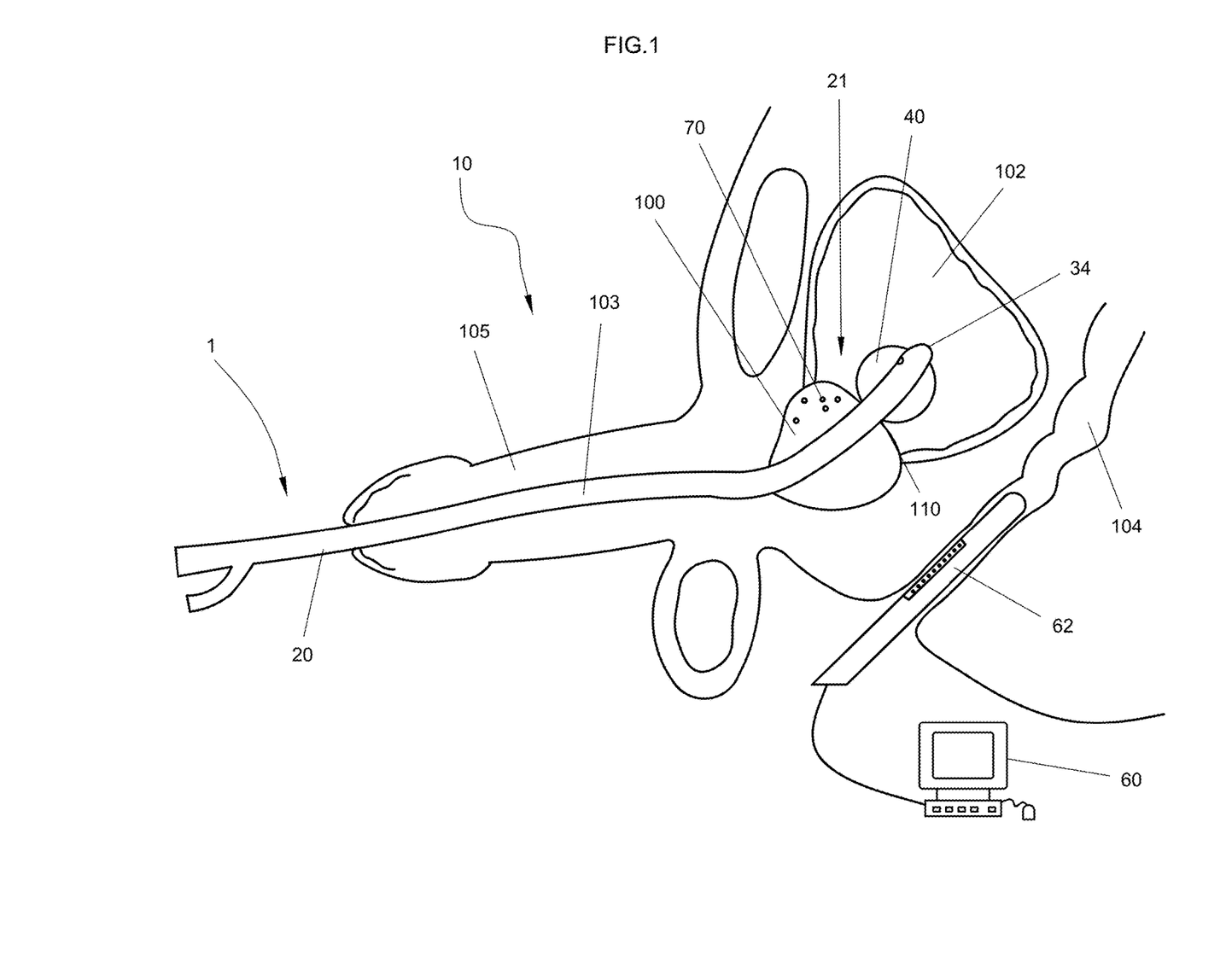
FIG. 1 is a detailed schematic illustration of the urethra identification system of the present invention operatively disposed relative to a patient.

As shown in FIG. 1, the present invention is directed towards an echo-opaque identification device or a urethra identification system, generally indicated as 10, and further to a method of identifying a patient's urethral anatomical course, in real time in order to aid in the precise placement of a treatment element into the patient's prostate 100. However, the present invention is not limited to this application and can be utilized to identify any other tubular anatomic structure. A desired method of the present invention relates to the effective placement of a brachytherapy radioactive seed and/or a cryoablation probe, with precision, at a desired location within the patient's prostate 100.

Looking first to the illustrated embodiment of the urethra identification system 10, the identification system 10 includes an echo-opaque catheter 1, such as a urethral catheter 1, and an imaging device 60. In particular, the echo-opaque catheter 1 includes an elongated flexible catheter shaft 20, which is similar in length to that of a traditional Foley catheter. The elongated flexible catheter shaft 20 of the urethral catheter 1 has a proximal portion 21, a proximal end 34 and a distal end 22. The urethral catheter 1 may be adapted from a Foley catheter or may be any other implantable catheter with similar dimensions and also can be referred to as an echo-opaque urethral catheter. The echo-opaque urethral catheter 1 having the elongated flexible shaft 20 is structured to be introduced into the urethra 103 of a patient through the penis 105 until a proximal tip or end 34 thereof extends into a urinary bladder 102 of the patient so as to drain urine from the urinary bladder 102.

Figure 2A:
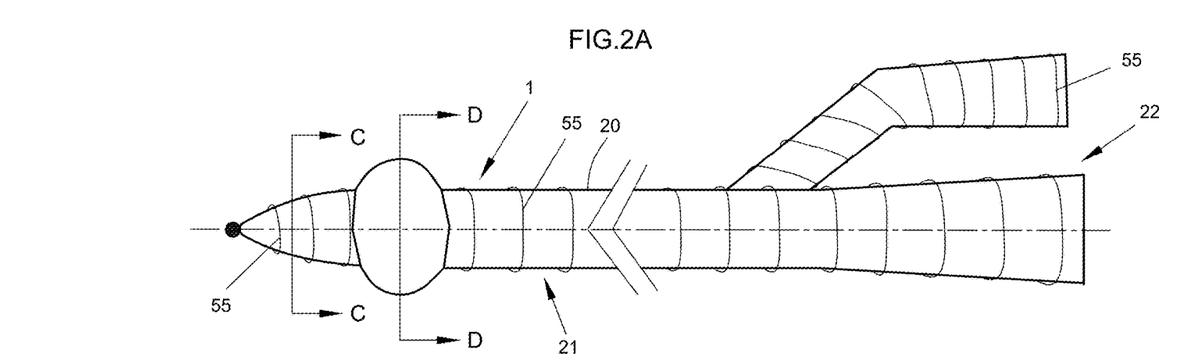
FIG. 2A is an illustrative view of one embodiment of the echo-opaque catheter of the present invention, wherein wires made of echogenic and radio-opaque materials enclose the catheter wall.
Figure 2B:
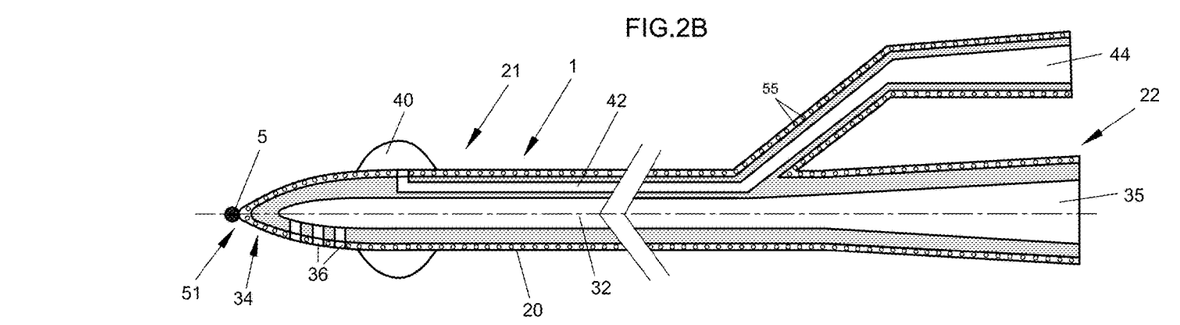
FIG. 2B is a longitudinal cross-sectional view of the same embodiment of the echo-opaque catheter as shown in FIG. 2A.

An embodiment of the present invention is shown in FIG. 2B. The flexible elongated shaft 20 of the echo-opaque urethral catheter 1 may include a primary lumen 32 that extends generally from the proximal end 34 that is inserted into the patient's urinary bladder 102 to an exterior, open end 35. In this manner, and through this primary lumen 32, urine may be drained from the patient's urinary bladder 102 into the urethral catheter 1 via holes 36 at the proximal end 34 during the performance of this and other procedures, as necessary, and/or after the procedure. Further provided in a desired embodiment of the echo-opaque urethral catheter 1 and located on the flexible elongated shaft 20 is a tip balloon 40, which may be located near the proximal end 34 of the flexible elongated shaft 20 of the echo-opaque urethral catheter 1. In particular, the tip balloon 40 is formed of a flexible material and is structured to be effectively expanded upon the introduction of a fluid therein. The fluid may be gas, liquid or a mixture of gas and liquid and may have enhanced radio-opaque and/or echogenic properties. In order to aid the inflation of the tip balloon 40, a secondary lumen 42 is provided in fluid flow communication between the tip balloon 40 and an inlet port 44. The inlet port 44 may include any desirable valve construction so as to effectively allow for the introduction of a fluid while regulating the escape of a fluid. In addition, a tip marker 5 may be attached near the proximal end 34 of the flexible elongated shaft 20 of the urethral catheter 1. The tip marker 5 may be made of hyper-echogenic and radio-opaque materials and may take a special form and shape, so that it would accurately indicate the position of the proximal end 34 of the elongated flexible shaft 20 of the echo-opaque urethral catheter 1 during insertion of treating elements even without aid of the inflation of the tip balloon 40. In use, the flexible elongated shaft 20 of the echo-opaque urethral catheter 1 is introduced into the patient's urethra 103 until the tip balloon 40 extends into the urinary bladder 102 of the patient. Once inserted into the urinary bladder 102 of the patient as indicated by the tip marker 5, the tip balloon 40 may thereafter be effectively inflated through the secondary lumen 42. Once the tip balloon 40 is inflated, as illustrated in FIG. 1, the echo-opaque urethral catheter 1 is essentially maintained in its operative and fluid flow connection with the urinary bladder 102 of the patient. Specifically, the larger size of the tip balloon 40 relative to the opening to the urethra 103 from the urinary bladder 102 is such that removal of the urethral catheter 1 is generally resisted. Furthermore, it is noted that although the tip balloon 40 is not a prerequisite for the echo-opaque urethral catheter 1 and for the urethra identification system 10 of the present invention, it may be desirable as it will provide a precise positioning of the echo opaque urethral catheter 1 within the patient.

Looking further to a desired echo-opaque urethral catheter 1, the flexible elongated shaft 20 of the urethral catheter 1 is structured to be partially or completely (FIGS. 2A-5D) echogenic and radio-opaque. Desirably, the whole flexible elongated shaft 20 of the urethral catheter 1 or at least the proximal half of the flexible elongated shaft 20 is structured to be echogenic and radio-opaque. This design takes out the guesswork involved in deciding the proper length and location of a portion of the flexible elongated shaft 20 of the urethral catheter 1 that may reside in the urethra 103 enclosed by the prostate 100 after insertion.

The echogenicity may be created by introducing bubbles into the walls 123 of the flexible elongated shaft 20 of the urethral catheter 1, using air or inert gases such as argon, nitrogen or helium. Also, metallic chips may be incorporated into the entire or at least the proximal portion 21 of the flexible elongated shaft 20 of the echo-opaque urethral catheter 1 to generate distinct ultrasound images. The bubbles or metallic chips are indicated by the numeral 23. Furthermore, sanded or corrugated metal wires 55 (FIGS. 2C-2D) or 56 (FIGS. 3C-3D) may also be inserted into the walls 123 (FIGS. 3B-3D) or placed on an outside surface 121 of the flexible elongated shaft 20 of the echo-opaque urethral catheter 1 (FIGS. 2B-2D) and thus generate landmark ultrasound images. The echogenic metals used can be selected from metal or metal alloys of aluminum, stainless steel, etc. As shown in FIGS. 4C-D and 5C-D, the echogenicity of the flexible elongated shaft 20 of the urethral catheter 1 may also be enhanced by coating the outside 121 or inside 120 surfaces (the surfaces are better seen on FIGS. 2D and 3D), of the whole of the flexible elongated shaft 20 of the echo-opaque urethral catheter 1 or at least the proximal portion 21 of it which will be inserted into the urethra 103 enclosed by the prostate 110 with echo-enhancing materials 56, such as magnesium, barium or polymers. Also, the echogenic material may be incorporated within the walls 123 of the flexible elongated shaft 20 of the urethral catheter 1 (FIGS. 3 C-3D). U.S. Pat. No. 6,749,554 to Snow et al. identifies a series of polymers that can enhance ultrasound visibility. The coating may be deposited into a pattern such as stripes to further create a distinct feature.

For X-ray visualization, radio-opaque materials 56 may be used to make or coat as the whole or at least a portion of the flexible elongated shaft 20 of the echo-opaque urethral catheter 1. Materials may be used include chemical compounds with radio-opaque properties such as iodine, iohexol, iothalamate, ioxaglate, iopamidol, ioversaol, metriazimide, and/or diatrizoates. Also, metal or metal alloys with radio-opaque characteristics may also be used, such as those containing barium, magnesium, bismuth, lead, gold, tungsten, silver, platinum, palladium, iridium or rhodium. Similarly, the radio-opaque materials 56 may be incorporated into (FIGS. 3B-3D) or used to coat the inside and outside surfaces 120 and 121 of the walls 123 of the flexible elongated shaft 20 of the echo-opaque urethral catheter 1 (FIGS. 4C-D and 5C-D). The coating may form special patterns that would generate even more distinguishable images.

Because some materials will enhance visualization of the echo-opaque urethral catheter 1 under both ultrasound and X-ray, it is desirable to use these materials. Also, the echogenic and radio-opaque coating materials 56 may be deposited on the inside 120 or outside 121 surfaces of the walls of the flexible elongated shaft 20 of the urethral catheter 1 (better shown on FIGS. 2C & 2D and FIGS. 3C & 3D). The flexible elongated shaft 20 of the urethral catheter 1 may be made of any biocompatible polymers and may take the shape of any regular "Foley Catheter". Further, the urethral catheter 1 may be a flexible catheter or a non-inflatable catheter.

As shown in FIG. 1, an echogenic and radiopaque image portion 110 of the flexible elongated shaft 20 of the echo-opaque urethral catheter 1 is aligned completely with the patient's urethra, which is enclosed within the prostate 100. Because the proximal half or the whole catheter is desirably echogenic and radiopaque, the physicians or technicians do not have to undertake extra imaging procedures to determine the length of the prostate 100 which may be used to determine the length and location of the echo-opaque portion of the catheter. Therefore, alignment is guaranteed.

Further, provided as part of the urethra identification system 10 of the present invention is an imaging device, generally indicated by the numeral 60. The imaging device 60 may include any of a number of different types of imaging devices which provide an accurate, real time view of internal organs, including yet to be developed imaging devices. In desired, illustrated embodiments, the imaging device 60 includes an ultrasound type system or an X-ray type machine. If it is an ultrasound type system, an imaging probe 62 is desirably provided and is structured to emit sound waves in a conventional fashion towards the prostate 100 so as to generate ultrasound images on an associated monitor and processor assembly. In use, the imaging probe 62 is desirably inserted into the rectum 104 of the patient as that provides a substantially close proximity to the prostate 100, and, as a result, also in close proximity to the echo-opaque urethral catheter 1 that is located within the prostate 100.

With the radio-opaque and echogenic image portion 110 of the flexible elongated shaft 20 of the echo-opaque urethral catheter 1 generally inserted into the urethra 103, an effective image can be achieved by the imaging device 60. In particular, it is noted that although the urethra 103 is generally not visible and/or readily discernable within the prostate 100 utilizing ultrasound and/or other standard imaging techniques, by inserting the echo-opaque urethral catheter 1 into the urethra 103, an acoustic or radio-opaque image is generated utilizing the imaging device 60. This identification of the urethra 103 may then be monitored during performance of a necessary procedure, such as the effective location of a treatment element 70 in the prostate 100.

As previously recited, in the preferred embodiment the treatment element 70 may include one or more radioactive seeds or probes. Alternatively, the treatment element 70 may include one or more cryo-probes and/or temperature sensing probes that are inserted into the prostate 100 of the patient in order to achieve effective cryoablation of a tumor that may be contained within the prostate 100 or treatment for BPH. In either such instances, however, effective positioning of the treatment element 70 within the prostate 100, taking into account a desired optimal spacing with the urethral wall can be achieved. Moreover, such placement may also impact the nature and/or extent of treatment, such by helping in the determination of the number of radioactive seeds to be used and/or the determination of the progress of BPH treatment.

Figure 2C:
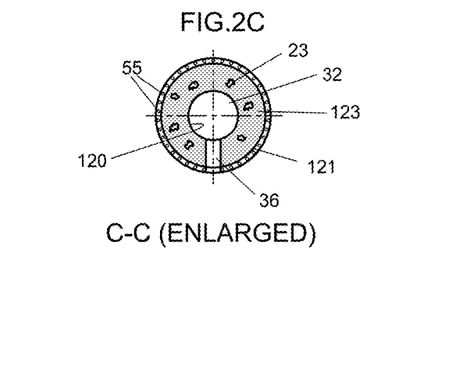
FIG. 2C is a cross-sectional view of the same embodiment of the echo-opaque catheter as shown in FIG. 2A along C-C axis.
Figure 2D:
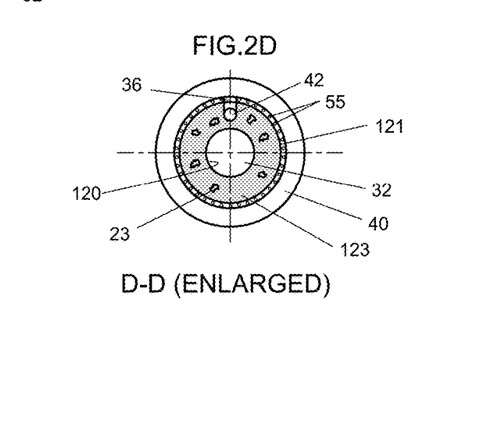
FIG. 2D is a cross-sectional view of the same embodiment of the echo-opaque catheter as shown in FIG. 2A along the D-D axis
Figures 3A, 3B:
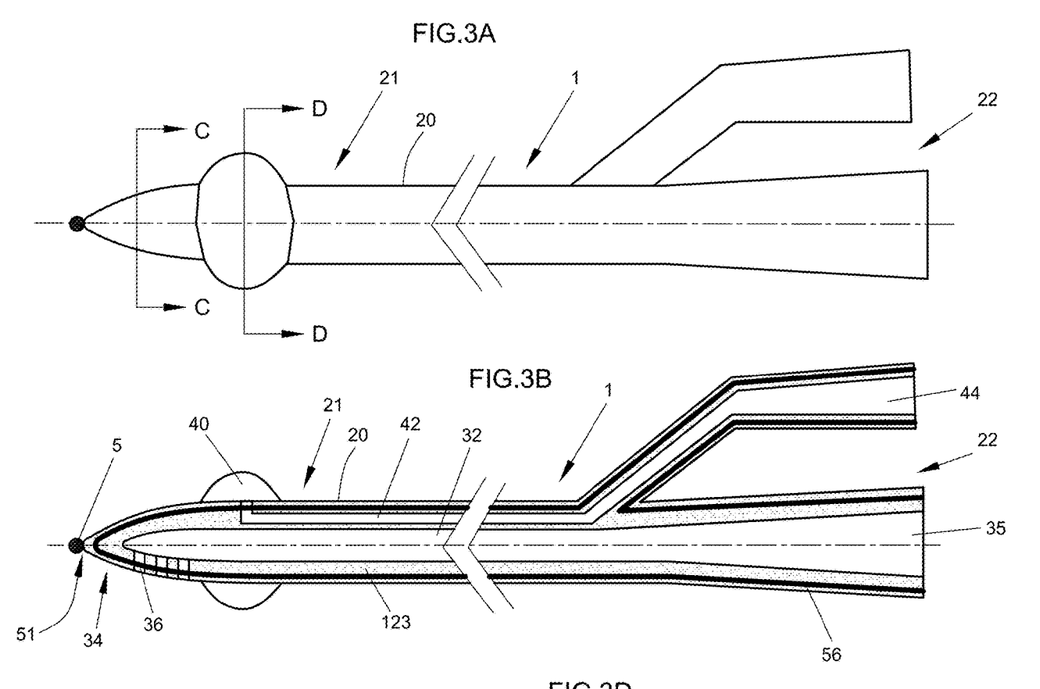
FIG. 3A is an illustrative view of one of embodiment of the echo-opaque catheter of the present invention, wherein echogenic and radio-opaque materials are deposited/incorporated within the catheter wall.
FIG. 3B is a longitudinal cross-sectional view of the same embodiment of the echo-opaque catheter as shown in FIG. 3A.
Figure 3C:
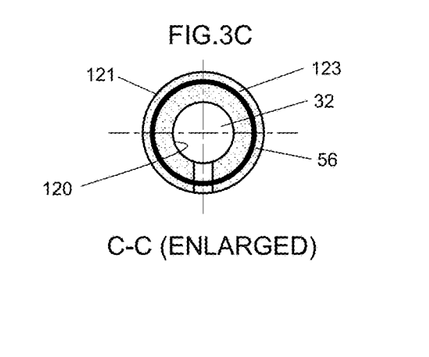
FIG. 3C is a cross-sectional view of the same embodiment of the echo-opaque catheter as shown in FIG. 3A along the C-C axis.
Figure 3D:
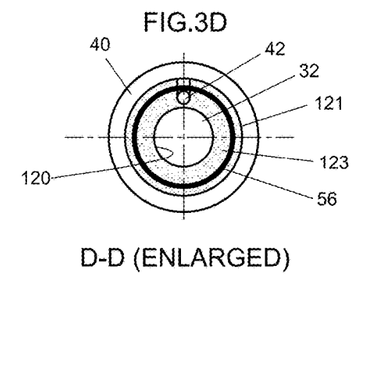
FIG. 3D is a cross-sectional view of the same embodiment of the echo-opaque catheter as shown in FIG. 3A along the D-D axis.
Figure 4A:
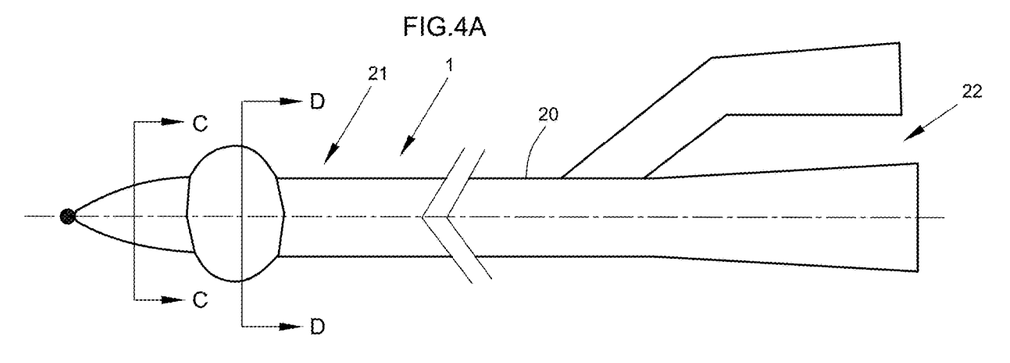
FIG. 4A is an illustrative view of one of embodiment of the echo-opaque catheter of the present invention, wherein the inside surface of the catheter is coated with echogenic and radio-opaque materials.
Figure 4B:
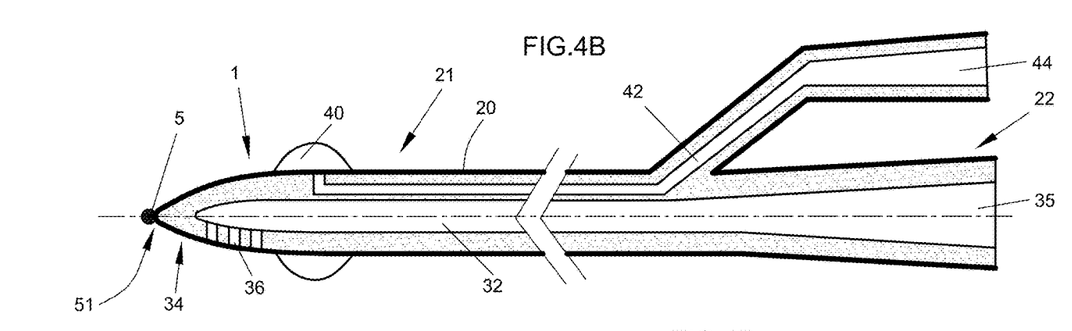
FIG. 4B is a longitudinal cross-sectional view of the same embodiment of the echo-opaque catheter as shown in FIG. 4A.
Figure 4C:
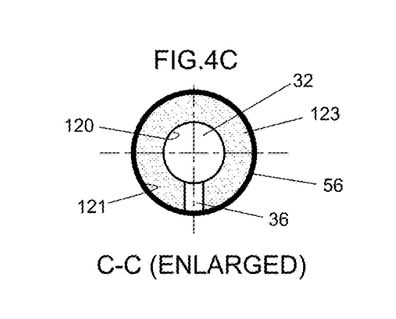
FIG. 4C is a cross-sectional view of the same embodiment of the echo-opaque catheter as shown in FIG. 4A along the C-C axis.
Figure 4D:
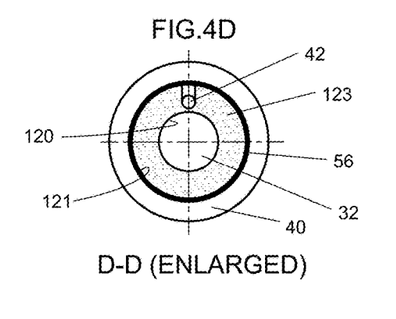
FIG. 4D is a cross-sectional view of the same embodiment of the echo-opaque catheter as shown in FIG. 4A along the D-D axis.
Figure 5A:
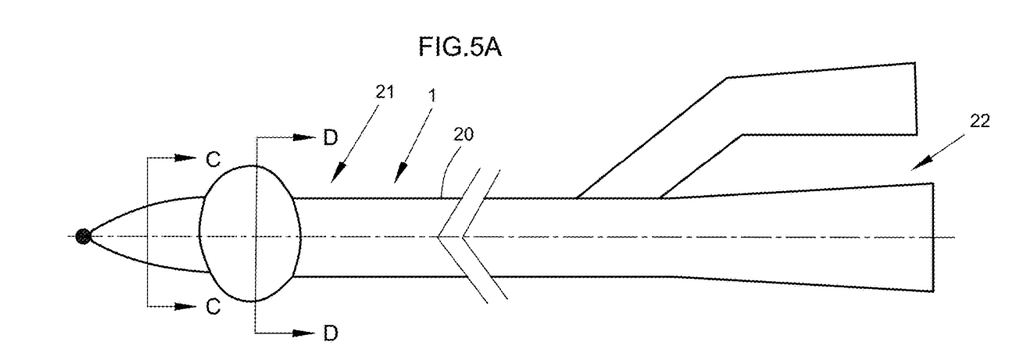
FIG. 5A is an illustrative view of one of embodiment of the echo-opaque catheter of the present invention, wherein the outside surface of the catheter is coated with echogenic and radio-opaque materials.
Figures 5B, 5C, 5D:
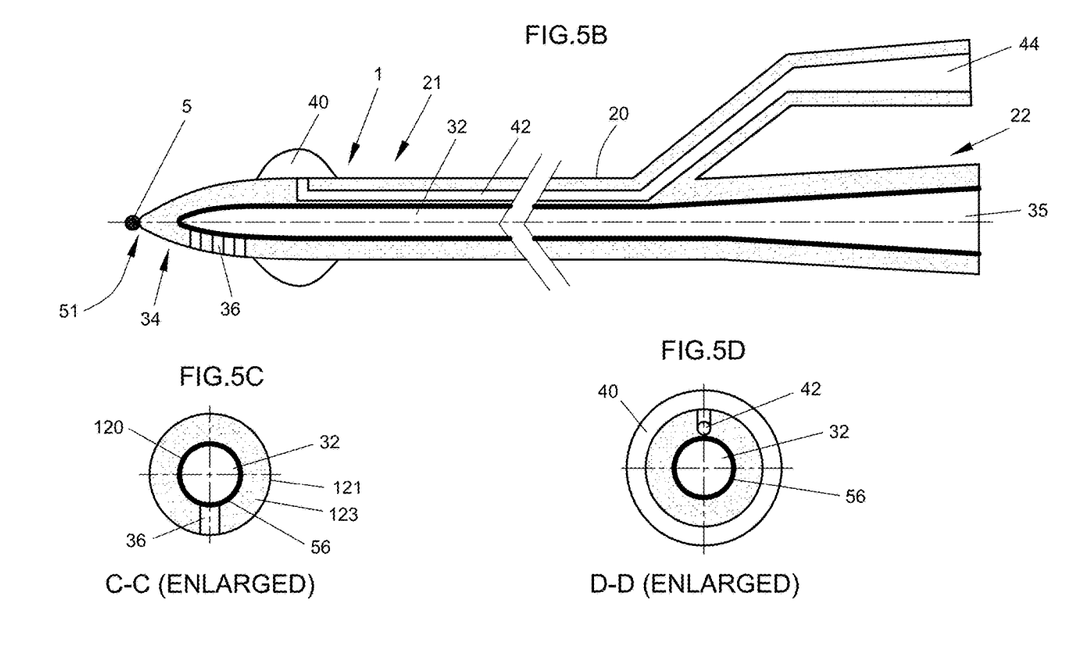
FIG. 5B is a longitudinal cross-sectional view of the same embodiment of the echo-opaque catheter as shown in FIG. 5A.
FIG. 5C is a cross-sectional view of the same embodiment of the echo-opaque catheter as shown in FIG. 5A along the C-C axis.
FIG. 5D is a cross-sectional view of the same embodiment of the echo-opaque catheter as shown in FIG. 5A along the D-D axis.

Referring to FIGS. 2B-2C, in an embodiment of the echo-opaque urethral catheter 1 of the present invention, hyper-echogenic and radio-opaque wires or pieces 55 may also be provided and disposed completely or partially around a periphery of the flexible elongated shaft 20 of the urethral catheter 1. These hyper-echogenic and radio-opaque metals of echo-opaque wires or pieces 55, such as hyper-echogenic rings 55, may be used to define the exterior of the flexible elongated shaft 20 of the urethral catheter 1. Specifically, the use of the hyper-echogenic rings 55 will exhibit visible landmark images when utilizing the imaging device 60, those landmarks also being potentially helpful for the selection of a treatment element 70 and/or the effective and appropriate positioning of a treatment element 70, as needed (FIG. 1).

Utilizing the preceding urethra identification system 10 and the echo-opaque urethral catheter 1, it is further seen that the present invention may be directed towards a method of identifying a patient's urethral anatomic course, in real time, for the precise placement of a treatment element 70 into the patient's prostate 100. In use, the present method may include an initial step of producing a flexible, elongated urethral catheter 1 at least partially echogenic and radio-opaque, having a tip 51, such as can include the tip marker 5, that is structured to be inserted into a patient's urethra 103 and in fluid communication with the urinary bladder 102 of the patient. In the following step, the imaging probe 62 of the imaging device 60 is operatively positioned relative to the treatment site of the prostate 100 and proximal portion of the urethra 103. The imaging device 60 is then activated so as to obtain a real time image of the treatment site of the prostate 100. The echo-opaque urethral catheter 1 is introduced into the urethra 103 until the echogenic and radio-opaque image portion 110 of the flexible elongated shaft 20 of the urethral catheter 1 reaches a portion of the urethra 103 located within the prostate 100. Once inserted, physicians or technicians may identify and view the urethra 103 using the imaging image device 60 while placing treatment elements 70 into a patient's prostate 100, based on the relative position of the urethra 103 as indicated by the echo-opaque urethral catheter 1. In some embodiments, the tip balloon 40 may be placed near the proximal portion 21 of the flexible elongated shaft 20 of the urethral catheter 1 and/or the tip marker 5 may be affixed to an end of the proximal portion 21, such as at the proximal end 34 of the flexible elongated shaft 20. The echo-opaque urethral catheter 1 is introduced into the urethra 103 of the patient until the image portion 110 is generally aligned with a treatment site of the prostate 100, and, in some embodiments until the tip balloon 40 is disposed within the urinary bladder 102. When appropriate, the tip balloon 40 may be effectively inflated thereby securing the urethral catheter 1 within the urethra 103 of the patient.

The present method further includes the step of placing the imaging probe 62 of an ultrasound machine in operative proximity to the image portion 110 of the flexible elongated shaft 20 of the echo-opaque urethral catheter 1, and generally in operative proximity to the prostate 100 that is desirably aligned therewith. This step in the method desirably includes the insertion of the ultrasound probe 62 into the rectum 104 of the patient, and ultimately activating the imaging device 60 so as to produce a real time image of the prostate 100 of the patient. In another embodiment, an X-ray type image device, as the imaging device 60 may be placed near the treatment site. The practitioner may then, desirably utilizing the X-ray imaging device 60, appropriately identify and view the urethra 103 and effective placement of a treatment element 70 can thereafter proceed. In one embodiment of the present method, the effective placement of the treatment element 70 includes the insertion of one or more elongate brachytherapy probes which allow for the positioning of radioactive seeds in operative proximity to a tumor located within the prostate 100. Utilizing the image that is identified and viewed utilizing the imaging device 60, appropriate relative positioning of the radioactive seeds between the exterior of the prostate 100, the urethra 103 and the tumor to be treated can appropriately be achieved. Further, in another embodiment of the present method, the treatment element 70 may include one or more cryoablation cryo-probes, as well as potentially one or more temperature sensing probes. In use, the temperature sensing probes and/or cryo-probes are introduced into the prostate 100 in effective operative proximity to a tumor or other treatment site within the prostate 100. Once the one or more cryoablation cryo-probes are effectively positioned, a series of freezing and thawing cycles may then take place, such as through the introduction of a cryogenic gas, such as argon gas, to create an ice ball at the tumor located within the prostate 100 and/or to treat the BPH. As a result, in either such embodiment and/or in any other embodiment wherein a treatment element, such as a microwave or other heating element, to treat BPH or another ailment associated with the prostate, must be effectively placed within the prostate 100, a practitioner need not unduly sacrifice the health and integrity of the urethra 103 in positioning the treatment element 70, but rather can now take into account the appropriate location, size and orientation of the urethra 103 within the prostate 100 when determining an ideal location for the treatment element 70.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents, and may extend to alternate imaging needs outside of the prostate context.

What is claimed is:

1. A urethral catheter, comprising:
a flexible elongated shaft configured for insertion into and interfacing alignment with an existing anatomic course of a urethra at a urethral wall, said flexible elongated shaft having a proximal end, a distal end, and a proximal portion including an image portion, said proximal portion being communicatively associated with said proximal end and said image portion being configured to interface and align with the urethral wall and identify an existing anatomic course of at least a portion of the urethra that passes through a prostrate or that passes through an area including a gynecological structure of a patient,
wherein at least said image portion of said proximal portion of said flexible elongated shaft includes both an echogenic material and a radio-opaque material on at least one of an inside surface, an outside surface or within a wall of said flexible elongated shaft bounded by the inside surface and the outside surface at least in said image portion of said proximal portion of said flexible elongated shaft, said echogenic material being configured on or within said flexible elongated shaft to respectively image by ultrasound imaging and said radio-opaque material being configured on or within said flexible elongated shaft to respectively image by X-ray imaging the urethral catheter when in interfacing alignment with the urethral wall of the existing anatomic course of the urethra to identify the anatomic course of the urethra at least in said image portion of said flexible elongated shaft in an area of the urethra that passes through the prostrate or that passes through the area including the gynecological structure of a patient, said image portion being a part of said flexible elongated shaft without an inflatable element and without an ablative element being associated with said image portion when said image portion is in interfacing alignment with the urethral wall, and said echogenic material and said radio-opaque material defining at least said image portion to facilitate only imaging of the existing anatomic course of the urethra to identify the existing anatomic course of the urethra without changing the existing anatomic course of the urethra and without ablating a portion of the urethra adjacent said image portion of said flexible elongated shaft.

2. The urethral catheter of claim 1, wherein:
the entire said flexible elongated shaft is comprised of said echogenic material and said radio-opaque material.

3. The urethral catheter of claim 1, wherein:
said proximal portion of said flexible elongated shaft further includes a plurality of gas bubbles as said echogenic material.

4. The urethral catheter of claim 3, wherein:
said gas bubbles comprise oxygen or an inert gas.

5. The urethral catheter of claim 1, wherein:
said echogenic material comprises hyper-echogenic rings.

6. The urethral catheter of claim 5, wherein:
said hyper-echogenic rings comprise wires.

7. The urethral catheter of claim 6, wherein:
the wires forming the hyper-echogenic rings are positioned on the outside surface of said flexible elongated shaft of the urethral catheter.

8. The urethral catheter of claim 1, wherein:
said echogenic material is selected from the group consisting of a metal, metal alloys of aluminum, stainless steel, copper, iron, silver, gold, cobalt, nickel, barium, magnesium and an echo-enhancing polymer.

9. The urethral catheter of claim 1, wherein:
said echogenic material comprises metallic chips, the metallic chips being incorporated into at least said proximal portion of said flexible elongated shaft of the urethral catheter, and the metallic chips being configured to generate distinct ultrasound images to facilitate imaging.

10. The urethral catheter of claim 9, wherein:
said echogenic material comprises said metallic chips being incorporated into the entire portion of said flexible elongated shaft of the urethral catheter, and the metallic chips being configured to generate distinct ultrasound images to facilitate imaging.

11. The urethral catheter of claim 1, wherein:
said radio-opaque material is selected from the group consisting of iodine, iohexol, iothalamate, ioxaglate, iopamidol, ioversaol, metriazimide, diatrizoates, barium, magnesium, bismuth, lead, gold, tungsten, silver, platinum, palladium, iridium and rhodium.

12. The urethral catheter of claim 1, wherein:
said proximal portion of said flexible elongated shaft includes a plurality of holes configured to drain urine from a patient's urinary bladder into the urethral catheter.

13. The urethral catheter of claim 1, wherein:
said echogenic material or said radio-opaque material includes a coating on at least one of the inside surface or the outside surface of at least said proximal portion of said flexible elongated shaft in a stripe pattern configured to facilitate imaging of the urethral catheter.

14. The urethral catheter of claim 1, wherein:
said echogenic material or said radio-opaque material includes a coating on at least one of the inside surface or the outside surface of at least a portion of said flexible elongated shaft along a length of said flexible elongated shaft in an area associated with the prostrate or in the area including the gynecological structure of a patient.

15. The urethral catheter of claim 1, further comprising:
an inflatable tip balloon disposed on said flexible elongated shaft adjacent said proximal end of said flexible elongated shaft, wherein said inflatable tip balloon is configured to be inserted through the urethra and into a urinary bladder of the patient.

16. The urethral catheter of claim 15, further comprising:
an inflation conduit disposed in fluid communication with said inflatable tip balloon, said inflatable tip balloon being configured for inflation to a size greater than an entrance to the urinary bladder from the urethra to resist removal of said flexible elongated shaft from the urethra.

17. The urethral catheter of claim 1, wherein:
said outside surface of at least said image portion of said proximal portion of said flexible elongated shaft includes said echogenic material and said radio-opaque material and is configured to be operatively disposed adjacent to the urethral wall of a prostatic portion of the urethra or adjacent to the urethral wall of a portion of the urethra that passes through the area including the gynecological structure and is configured to identify the existing anatomic course of at least the portion of the urethra that passes through the prostrate or that passes through the area including the gynecological structure of the patient.

18. The urethral catheter of claim 1, further comprising:
a tip marker positioned on said proximal end of said flexible elongated shaft, said tip marker being configured to indicate a position of said proximal end of said flexible elongated shaft upon being positioned within a urinary bladder of the patient and to facilitate positioning of a treatment element at a treatment site relative to the urethra.

19. The urethral catheter of claim 18, wherein:
said tip marker is comprised of said echogenic material and said radio-opaque material.

20. The urethral catheter of claim 19, further comprising:
an inflatable tip balloon disposed on said flexible elongated shaft adjacent said proximal end of said flexible elongated shaft, wherein said inflatable tip balloon is configured to be inserted through the urethra and into the urinary bladder of the patient,
wherein said tip marker is located at a position proximal relative to a position of said inflatable tip balloon on said flexible elongated shaft of the urethral catheter.

21. A urethral catheter, comprising:
a flexible elongated shaft configured for insertion into and interfacing alignment with an existing anatomic course of a urethra at a urethral wall, said flexible elongated shaft having a proximal end, a distal end, and a proximal portion including an image portion, said proximal portion being communicatively associated with said proximal end and said image portion being configured to interface and align with the urethral wall and identify the existing anatomic course of at least a portion of the urethra that passes through a prostrate or that passes through an area including a gynecological structure of a patient; and
an echogenic material and a radio-opaque material, said echogenic material and said radio-opaque material being included with at least said image portion of said proximal portion of said flexible elongated shaft, said echogenic material being configured to respectively image by ultrasound imaging and said radio-opaque material being configured to respectively image by X-ray imaging at least said image portion of said proximal portion of said flexible elongated shaft when in interfacing alignment with the urethral wall of the existing anatomic course of the urethra to identify at least the existing anatomic course of the urethra in an area of the urethra that passes through the prostrate or that passes through the area including the gynecological structure of the patient, said image portion being a part of said flexible elongated shaft without an inflatable element and without an ablative element being associated with said image portion when said image portion is in interfacing alignment with the urethral wall, and said echogenic material and said radio-opaque material defining at least said image portion to facilitate only imaging of the existing anatomic course of the urethra to identify the existing anatomic course of the urethra without changing the existing anatomic course of the urethra and without ablating a portion of the urethra adjacent said image portion of said flexible elongated shaft.

22. The urethral catheter of claim 21, wherein:
said radio-opaque material is selected from the group consisting of iodine, iohexol, iothalamate, ioxaglate, iopamidol, ioversaol, metriazimide, diatrizoates, barium, magnesium, bismuth, lead, gold, tungsten, silver, platinum, palladium, iridium and rhodium; and
said echogenic material is selected from the group consisting of a metal, metal alloys of aluminum, stainless steel, copper, iron, silver, gold, cobalt, nickel, barium, magnesium and an echo-enhancing polymer.

23. A urethral catheter, comprising:

a flexible elongated shaft configured for insertion into and interfacing alignment with an existing anatomic course of a urethra at a urethral wall, said flexible elongated shaft having a proximal end, a distal end, and a proximal portion including an image portion, said proximal portion being communicatively associated with said proximal end and said image portion being configured to interface and align with the urethral wall and identify the existing anatomic course of at least a portion of the urethra that passes through a prostrate or that passes through an area including a gynecological structure of a patient; and a tip marker positioned on said proximal end of said flexible elongated shaft, said tip marker being configured to indicate a position of said proximal end of said flexible elongated shaft upon being positioned within a urinary bladder of the patient and to facilitate positioning of a treatment element at a treatment site relative to the urethra, wherein at least said image portion of said proximal portion of said flexible elongated shaft is without an inflatable element and without an ablative element when said image portion is in interfacing relation with the urethral wall and includes an echogenic material and a radio-opaque material, said echogenic material and said radio-opaque material defining at least said image portion to facilitate only imaging of the existing anatomic course of the urethra to identify the existing anatomic course of the urethra without changing the existing anatomic course of the urethra and without ablating a portion of the urethra adjacent said image portion of said flexible elongated shaft, and said echogenic material being configured to respectively image by ultrasound imaging and said radio-opaque material being configured to respectively image by X-ray imaging at least said image portion of said proximal portion of said flexible elongated shaft when in interfacing alignment with the urethral wall of the anatomic course of the urethra to identify at least the existing anatomic course of the urethra that passes through the prostrate or that passes through the area including the gynecological structure of the patient.

24. The urethral catheter of claim 23, wherein:

said tip marker is comprised of said echogenic material and said radio-opaque material.

25. The urethral catheter of claim 24, further comprising:

an inflatable tip balloon disposed on said flexible elongated shaft adjacent said proximal end of said flexible elongated shaft, wherein said inflatable tip balloon is configured to be inserted through the urethra and into the urinary bladder of the patient, wherein said tip marker is located at a position proximal relative to a position of said inflatable tip balloon on said flexible elongated shaft of the urethral catheter.

26. A urethral catheter, comprising:

a flexible elongated shaft configured for insertion into and interfacing alignment with an existing anatomic course of a urethra at a urethral wall, said flexible elongated shaft having a proximal end, a distal end, and a proximal portion associated with said proximal end, said proximal portion including an image portion, wherein at least said proximal portion of said flexible elongated shaft is comprised of both an echogenic material and a radio-opaque material, said echogenic material and said radio-opaque material being formed on at least one of an inside surface or an outside surface of said proximal portion, or incorporated within a wall bounded by the inside surface and the outside surface of said proximal portion, said echogenic material and said radio-opaque material respectively facilitating imaging by ultrasound or X-ray of the urethral catheter at least in an area of the urethra adjacent to the prostrate when said flexible elongated shaft is in interfacing alignment with the urethral wall, said echogenic material and said radio-opaque material defining at least said image portion to facilitate only imaging of the existing anatomic course of the urethra to identify the existing anatomic course of the urethra without changing the existing anatomic course of the urethra and without ablating a portion of the urethra adjacent said image portion of said flexible elongated shaft, wherein said image portion of said proximal portion of said flexible elongated shaft is without an inflatable element and without an ablative element when said image portion is in interfacing relation with the urethral wall, wherein said proximal portion of said flexible elongated shaft containing said echogenic material and said radio-opaque material comprise wires forming hyper-echogenic rings, and wherein said wires forming said hyper-echogenic rings are sanded or corrugated.

* * * * *